United States Patent
Greeley et al.

(10) Patent No.: US 12,303,189 B2
(45) Date of Patent: May 20, 2025

(54) ENERGIZED CORERS WITH ENERGIZED INTERNALS

(71) Applicant: Medtronic Advanced Energy LLC, Minneapolis, MN (US)

(72) Inventors: Roger D. Greeley, Portsmouth, NH (US); Bradley W. Jacobsen, Erie, CO (US); Xiaoming Cheng, Keller, TX (US); Amy Bradley, Westford, MA (US); Yeung Chow, Longmont, CO (US); Anjali Dhiman, Commerce City, CO (US); Yahia Laouar, Superior, CO (US); Prakash Manley, Arvada, CO (US); Martin Masson, Keller, TX (US); Molly Ann Megna, Denver, CO (US); Katherine M. Puckett, Denver, CO (US); Wade Schutte, Denver, CO (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 848 days.

(21) Appl. No.: 17/392,889

(22) Filed: Aug. 3, 2021

(65) Prior Publication Data

US 2023/0039545 A1 Feb. 9, 2023

(51) Int. Cl.
*A61B 18/14* (2006.01)
*A61B 18/00* (2006.01)
*A61B 18/12* (2006.01)

(52) U.S. Cl.
CPC ...... *A61B 18/1487* (2013.01); *A61B 18/1482* (2013.01); *A61B 2018/0016* (2013.01); *A61B 2018/00577* (2013.01); *A61B 2018/00601* (2013.01); *A61B 2018/00922* (2013.01); *A61B 2018/1253* (2013.01);
(Continued)

(58) Field of Classification Search
CPC ............ A61B 18/1487; A61B 18/1482; A61B 2018/0016; A61B 2018/00577; A61B 2018/601; A61B 2018/00922; A61B 2018/1253; A61B 2018/142;
(Continued)

(56) References Cited

U.S. PATENT DOCUMENTS

| 5,215,521 A | 6/1993 | Cochran et al. |
| 6,517,498 B1 * | 2/2003 | Burbank .......... A61B 17/32056 606/45 |

(Continued)

OTHER PUBLICATIONS

International Search Report and Written Opinion from PCT Application PCT/IB2022/057219, dated Nov. 10, 2022, 15 pgs.
(Continued)

*Primary Examiner* — Linda C Dvorak
*Assistant Examiner* — Abigail Bock
(74) *Attorney, Agent, or Firm* — Husch Blackwell LLP (57) ABSTRACT

An electrosurgical device including an elongated body extending from a proximal portion to a distal portion and defining an internal passageway configured to convey tissue from the distal portion to the proximal portion, and a coring electrode positioned at the distal portion of the elongated body, where the coring electrode is at an opening to the internal passageway, and where the coring electrode is configured to deliver electromagnetic energy to adjacent tissue to cut a volume of the tissue as the tissue is conveyed into the internal passageway.

24 Claims, 10 Drawing Sheets

(52) U.S. Cl.
CPC ... *A61B 2018/126* (2013.01); *A61B 2018/142* (2013.01); *A61B 2018/1467* (2013.01); *A61B 2218/002* (2013.01); *A61B 2218/007* (2013.01)

(58) Field of Classification Search
CPC ...... A61B 2018/1467; A61B 2218/002; A61B 2218/007
See application file for complete search history.

(56) References Cited

U.S. PATENT DOCUMENTS

| | | | | |
|---|---|---|---|---|
| 7,241,293 | B2* | 7/2007 | Davison | A61B 18/1402 604/35 |
| 8,177,783 | B2* | 5/2012 | Davison | A61B 18/1402 606/41 |
| 9,023,040 | B2* | 5/2015 | Bloom | A61B 18/1492 606/41 |
| 2001/0001124 | A1 | 5/2001 | Mueller | |
| 2002/0143289 | A1* | 10/2002 | Ellis | A61F 2/2493 606/41 |
| 2002/0193705 | A1* | 12/2002 | Burbank | A61B 90/17 600/564 |
| 2005/0165345 | A1 | 7/2005 | Laufer | |
| 2013/0220524 | A1 | 8/2013 | Zeroni et al. | |
| 2014/0277039 | A1 | 9/2014 | Liberatore | |
| 2016/0278844 | A1* | 9/2016 | Zamarripa | A61B 18/1482 |
| 2017/0303995 | A1* | 10/2017 | Garrison | A61B 18/1206 |
| 2020/0330156 | A1 | 10/2020 | Brown et al. | |

OTHER PUBLICATIONS

International Search Report and Written Opinion from PCT Application PCT/IB2022/057172, dated Nov. 10, 2022, 15 pgs.

Application and file history for U.S. Appl. No. 17/392,849, filed Aug. 3, 2021, inventors Cheng et al.

* cited by examiner

ENERGIZED CORERS WITH ENERGIZED INTERNALS

FIELD

This invention relates generally to surgical methods and apparatuses and particularly to electrosurgical devices.

BACKGROUND

Electrosurgical devices such as plasma-mediated thermoelectric cutting devices have been developed for use in cutting soft biological tissue in surgical settings. Such devices have found use in various surgical settings and procedures including, but not limited to, spine discectomy and fusion, and other surgical specialties such as general surgery, breast, thoracic, general surgeries and the like. Typically, such electrosurgical devices are classified as being either a monopolar or bipolar electrosurgical devices. A monopolar device generally includes a single electrode on the device and configured to communicate with a reference electrode, typically in the form of a pad, attached to the exterior of a patient. Monopolar electrosurgical devices deliver highly concentrated electrical energy that enhances cutting edges to excise material and then transmits through the tissue of a patient. In contrast, a bipolar electrosurgical device includes a pair of electrodes on the device and positioned in close proximity to one another. Bipolar electrosurgical devices may utilize lower energy levels, compared to monopolar devices, and may be better suited for heating or coagulation. Further, bipolar electrosurgical devices may be better suited for wet field application and localized heating.

SUMMARY

The techniques of this disclosure generally relate to electrosurgical cutting devices with a coring tip that can be adapted for monopolar or bipolar functionality. The disclosed devices may also include one or more additional electrodes configured to help excise and remove material without clogging. While the devices may be used in a variety of surgical procedures, the disclosed devices may be particularly suited for discectomy procedures or those where preservation of tissue directly adjacent to the cutting site is important for success of the procedure.

In an embodiment, the disclosure describes system including an electrosurgical device including an elongated body extending from a proximal portion to a distal portion and defining an internal passageway configured to convey tissue from the distal portion to the proximal portion, and a coring electrode positioned at the distal portion of the elongated body, where the coring electrode is at an opening to the internal passageway, and where the coring electrode is configured to deliver electromagnetic energy to adjacent tissue to cut a volume of the tissue as the tissue is conveyed into the internal passageway. In some embodiments, the disclosed electrosurgical device may further include an internal electrode positioned within the internal passageway and configured to deliver electromagnetic energy to the volume of the tissue to further cut or reduce a size of the volume of the tissue.

In another embodiment, the disclosure describes system including an electrosurgical device including an elongated body extending from a proximal portion to a distal portion and defining an internal passageway configured to convey tissue from the distal portion to the proximal portion, and a coring electrode positioned at the distal portion of the elongated body, where the coring electrode is at an opening to the internal passageway, wherein the coring electrode is configured to deliver electromagnetic energy to adjacent tissue to cut a volume of the tissue as the tissue is conveyed into the internal passageway, and where the coring electrode is longitudinally offset from a distal end of the elongated body so that a distal most surface of electrosurgical device is not defined by the coring electrode.

In another embodiment, the disclosure describes a method of performing electrosurgery on soft tissue including delivering electromagnetic energy to adjacent tissue using a coring electrode of an electrosurgical device to cut a volume of the tissue, where the electrosurgical device comprises an elongated body extending from a proximal portion to a distal portion and defining an internal passageway configured to convey tissue from the distal portion to the proximal portion, the a coring electrode positioned at the distal portion of the elongated body, and an internal electrode positioned within the internal passageway, where the coring electrode cuts the volume of the tissue as the tissue is conveyed into the internal passageway, and delivering electromagnetic energy using the least one internal electrode to further cut or reduce the size of the volume of the tissue cut by the coring electrode to facilitate the conveyance of the volume of the tissue through the internal passageway.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

The disclosure can be more completely understood in consideration of the following detailed description of various embodiments of the disclosure, in connection with the accompanying drawings, in which.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

Figure 1:
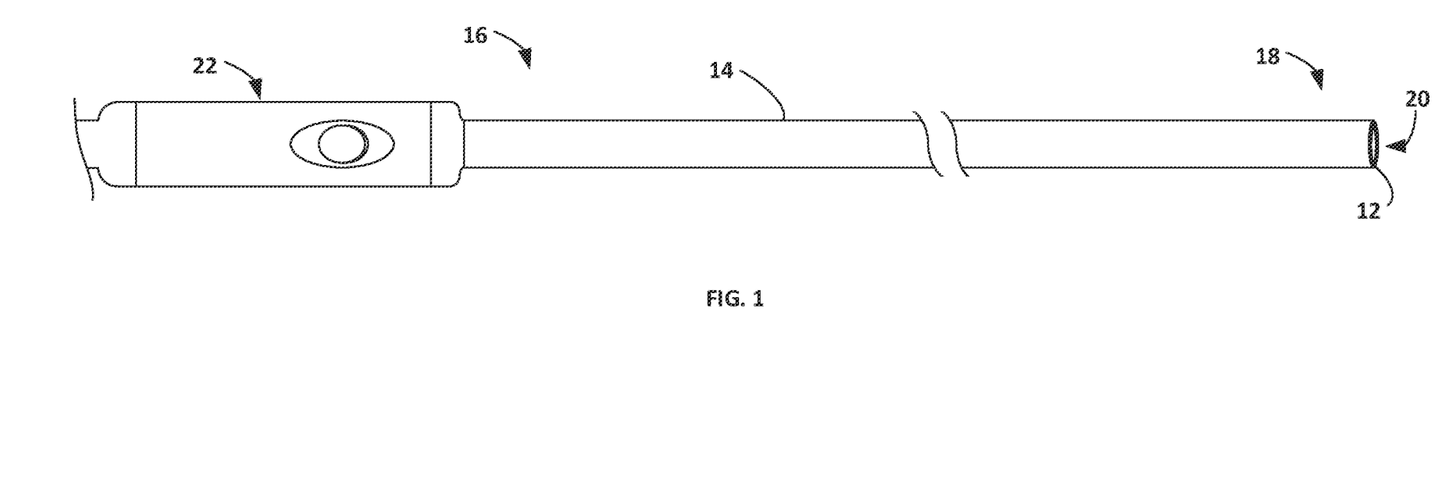
FIG. 1 is a schematic view of an example electrosurgical device that includes a coring electrode tip.

FIG. 1 is a schematic view of an example electrosurgical device 10 as described herein that includes a coring electrode 12 tip and may be used with electrosurgical procedures including, for example, performing a discectomy. A discectomy procedure involves the surgical removal of an intervertebral disc and fusion of adjacent vertebra. Intervertebral discs are flexible pads of fibro cartilaginous tissue tightly fixed between the vertebrae of the spine. The discs comprise a flat, circular capsule roughly 1 to 2 inches in diameter and about 0.25 to 0.5 inches thick and made of a tough, fibrous outer membrane called the annulus fibrosus, surrounding an elastic core called the nucleus pulposus. Under stress, it is possible for the annulus fibrosus to fail or the nucleus pulposus to swell and herniate, pushing through a weak spot in the annulus fibrosus membrane of the disc and into the spinal canal. Consequently, all or part of the annulus fibrosus and/or nucleus pulposus material may protrude through the weak spot, causing pressure against surrounding nerves which results in pain and immobility.

Where a damaged intervertebral disc must be removed from the patient as part of a discectomy and a subsequent fusion of vertebral bodies of the superior and inferior vertebrae, the surgeon may first retract soft tissue from the point of entry to the vertebrae to be fused. Around and attached to the vertebrae are, among other things, various muscles which act on the vertebrae to affect movement of the upper body. Once the retraction is complete, and the disc is exposed, the disc may be removed. The vertebrae may then be aligned to straighten the spinal column, and stabilized relative to one another by rods or other supports which are attached to the vertebrae by numerous fastening techniques. The surgeon may then place implants and bone grafts across the exposed surfaces of adjoining vertebrae and restore the location of the soft tissue to cover the bone graphs and vertebrae. The grafts regenerate, grow into bone and fuse the vertebrae together, with the implant and rod functioning as a temporary splint which stabilizes the spinal column while the bone fuses together over a period of months.

During the discectomy and fusion, the disclosed devices may be particularly useful to separate and remove the intervertebral disc without damage to the adjacent tissue and bone. Further, during a discectomy, blood vessels are often cut, ruptured or otherwise severed. These blood vessels bleed, and the resulting blood can flow into the tissue treatment site making visibility more difficult and prolonging the procedure. In some examples, the devices may also be used to shrink and seal blood vessels of the vertebral venous and/or arterial systems against blood loss before or after the vessels are cut, rupture or are otherwise severed.

Electrosurgical device 10 includes an elongated body 14 extending from a proximal portion 16 to a distal portion 18 that defines an internal passageway 20 configured to convey excised tissue from distal portion 18 to the proximal portion 16. Electrosurgical device 10 may be configured such that proximal portion 16 of elongated body couples with a handle assembly 22, which in turn is configured to couple to an electrosurgical power supply (not shown) that delivers the electromagnetic energy to coring electrode 12. The electrosurgical power supply may be configured to generate and provide radiofrequency (RF) monopolar energy, bipolar energy, or the option to select between either. Handle assembly 22 may also include one or more finger switches or buttons 26 for activating device 10 to deliver the desired electrosurgical energy to the adjacent tissue via one or more of the disclosed electrodes. Additionally, or alternatively, handle assembly 22 can include a stand or mount for stabilizing device 10 during an electrosurgical procedure. additional switches or buttons for actuating other features of device 10, additional connectors for coupling device 10 to other components (e.g., negative pressure pump and reservoir) for use during the procedure, and the like.

Coring electrode 12 is positioned along distal portion 18 of elongated body 14 and configured to deliver electromagnetic energy (e.g., RF plasma, including a pulsed electron avalanche plasma, or ablation energy) to surrounding patient tissue (e.g., soft tissue or disc material) to cut a volume of the tissue as the tissue is conveyed (e.g., suctioned toward) into internal passageway 20 and the cut volume of the tissue is further conveyed through internal passageway 20. In some examples, the opening that provides entry to internal passageway 20 may defined at least in part by the geometry of coring electrode 12. As electromagnetic energy is delivered to the surrounding soft tissue, coring electrode 12 cuts the adjacent tissue to create a volume of the tissue (e.g., excised tissue) that enters through the opening defined by coring electrode 12 and is conveyed into internal passageway 20.

Coring electrode 12, as well as the other electrodes described herein, may be composed of any suitable conductive material including, but not limited to, stainless steel, titanium, platinum, iridium, niobium or alloys thereof. Other components of device 10, including elongated body 14, can be fabricated from biologically acceptable materials suitable for medical applications, including metals, synthetic polymers, ceramics, and combinations thereof. For example, the components of elongated body 14 can be fabricated from materials such as stainless steel alloys, thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), semi-rigid and rigid materials, elastomers, rubbers, thermoplastic elastomers, thermoset elastomers, elastomeric composites, rigid polymers including polyphenylene, polyamide, polyimide, polyetherimide, polyethylene, and combinations thereof. Preferably, elongated body 14 is constructed to produce a rigid or resilient body capable of withstanding the longitudinal forces applied by the clinician during tissue removal without bending or kinking elongated body 14. Further, exposed surfaces of elongated body 14 (apart from the surfaces produced by the electrodes) should be electrically insulated from the disclosed electrodes. In some embodiments, the efficiency of energy delivery into tissue may be further regulated by the strategic use of coating materials such as ceramic, glass, or dielectric coatings to electrically insulate portions of the described electrodes or portions of elongated body 14 to control the surface area or separation distance between one or more electrodes.

Depending on the configuration of electrosurgical device 10 coring electrode 12 may be configured as a monopolar electrode or bipolar electrode, or configured to operate in either configuration depending on user selection. For example, coring electrode 12 may communicate with a reference electrode (not shown) such as a back plate, or topical pad connected to electro surgical power supply to provide a monopolar arrangement. Additionally, or alternatively, coring electrode 12 may communicate with one or more of the other electrodes on elongated body 14 that are described further below to provide an arrangement for the delivery of the electromagnetic energy in a bipolar configuration. As used herein, the term "reference electrode" is used to signify an electrode configured to communicate with one of the electrodes on elongated body 14 in a monopolar arrangement and is itself not carried by elongated body 14. Similarly, when an electrode is said to function in a monopolar arrangement, the electrode is configured to communicate with a reference electrode that is not carried by elongated body 14. The electromagnetic energy may be delivered in the form of radio frequency or pulsed radio frequency energy delivery to cut through surrounding soft tissue.

In a monopolar electrosurgical configuration, the active electrode, such as coring electrode 12, is positioned at the target surgical site. The reference electrode such as a dispersive pad, may be placed somewhere on the patient's body. Electrical current passes through the patient as it completes the electrical circuit from the active electrode to the reference electrode. The reference electrode has a much larger conductive surface area compared to the active electrode to help safely dissipate the electrical energy and prevent localized heating. In contrast, the active electrode has a much smaller surface area allowing for significant plasma or current to be produced at the treatment site to produce cutting, ablation, or coagulation affects. The electric current may be concentrated in the area of contact of the active electrode offering versatility and function with a variety of electrosurgical waveforms to produce different tissue effects. Monopolar electrosurgical configuration may be particularly useful in dry field plasma cutting and may be extended to wet field plasma cutting via waveform modification.

In a bipolar electrosurgical configuration, both the electrodes (e.g., active and return) are positioned in close proximity to one another at the target treatment site. Only the tissue spanning the distance between the two electrodes becomes included in the electrical circuit. Bipolar electrosurgery may offer advantages by permitting operation in a variety of mediums including wet field operation. In a wet field application, current may flow not only through the tissue but also through the fluid surrounding the tissue, and thus more energy will be dispersed at the site. The additional energy in wet field applications may permit coagulation or sealing in such environments. Further, the close proximity of the bipolar electrodes provides advantages in monitoring various properties of the adjacent tissue (e.g., tissue electrical resistivity and impedance) to provide more accurate an assessment of the adjacent tissue integrity, composition, or both.

During operation, coring electrode 12 defines a cutting edge. However, in contrast to the mechanical edge for a knife, the cutting edge of coring electrode 12 focuses the electric field induced by the applied electrical signal to generate a local plasma or current discharge. Hence the edge produced by coring electrode 12 may be tapered, rounded, flat, or sharp, but need not be of any particular dimension or sharpness. The tissue cutting may be assisted by mechanical force supplied by the clinician, the shape and configuration of coring electrode 12 providing tactile feedback to the user.

In some embodiments, particularly in use of discectomy procedures that include delicate adjacent tissue, to help decrease heat accumulation and associated collateral tissue damage, low voltage, current, power and/or low duty cycle waveforms may be used. Low power waveforms typically refer to low voltage, continuous waveforms. Low duty-cycle here typically refers to the proportion of time that the energy is actually being applied and may include cycles of less than 10% which may be, for instance, 1% or less, or 0.1% or less. A pulsed low duty-cycle signal may include a plurality of pulse bursts that are separated by more than one millisecond (e.g., has a frequency of less than 1 kHz) where each burst is shorter than one millisecond which may assist in minimizing tissue charring or burning.

The electrical signals suitable to create a plasma cutting effect are well known in the field. For instance, in the example of an applied RF (radio frequency) signal, the signal may have a frequency in the range of 100 kHz to 10 MHz applied in continuous, burst, or pulsed waveforms. Each burst typically has a duration in the range of 10 microseconds to 1 millisecond with each burst having a duty duration of about 0.1 to 10 microseconds. The pulses may be bi-phasic square waves that alternate positive and negative amplitudes. The interval between pulses should be shorter than a lifetime of the plasma vapor cavity in order to maintain the cavity and the plasma regime during each pulse burst. The time between the pulse bursts is sufficient so that the duty-cycle is relatively low. This minimizes the undesirable heating effects. Additional details regarding bipolar versus monopolar electrode selections and cutting versus coagulation operational parameters are described in U.S. Pat. No. 8,177,783 B2 entitled "Electric plasma-mediated cutting and coagulation of tissue and surgical apparatus," the entire contents of which is incorporated by reference.

Figure 2A:
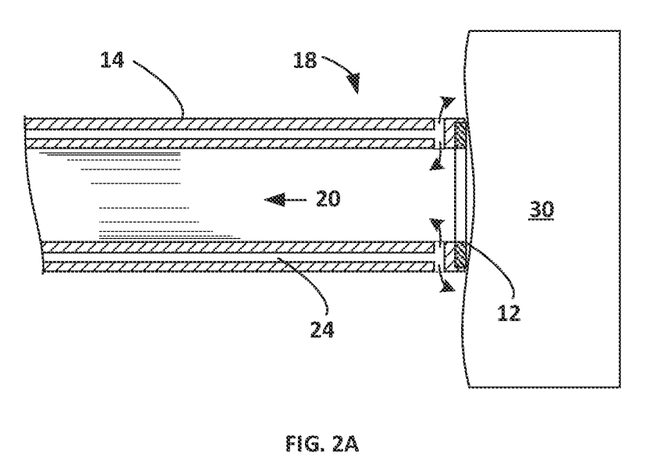
FIGS. 2A and 2B are schematic cross-sectional views of a distal portion of an elongated body illustrating cutting features of a coring electrode that may be used with the electrosurgical device of FIG. 1.
Figure 2B:
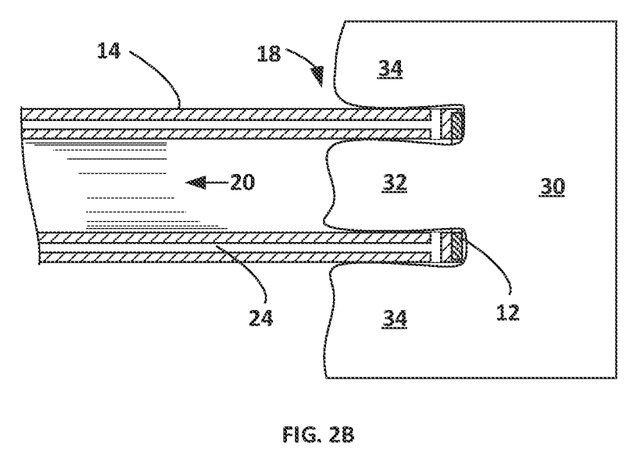

FIGS. 2A and 2B are schematic cross-sectional views of distal portion 18 illustrating cutting features of coring electrode 12 during operation. The configuration of coring electrode 12 defines an opening that provides entry into internal passageway 20. As electromagnetic energy is delivered to the surrounding soft tissue 30, coring electrode 12 cuts the adjacent tissue 30 to create a volume of the tissue (e.g., excised tissue 32) that enters through the opening defined by coring electrode 12 and is conveyed into internal passageway 20. Excised tissue 32 may be separated from tissue 30 by various means including briefly pausing forward motion and allowing the energy to cut across the inner radius of electrode 12 or slightly tilting or transversely moving electrode 12 to cut the base of 32. The adjacent tissue 34 is preserved and passes along the exterior elongated body 14.

To help facilitate conveyance of excised tissue 32 along internal passageway 20, proximal portion 16 (e.g., via handle assembly 22) may be coupled to a negative pressure source to provide suction and collection of the excised material. However, as excised tissue 32 is drawn into internal passageway 20, it may produce an occlusion within internal passageway 20 resulting in the creation of a larger than desired negative pressure or a delay in the electrosurgical procedure as the clinician must clear the passageway before the procedure may continue. In some embodiments, to help facilitate removal of excised tissue 32, the surface of internal passageway 20 may be coated or treated to prevent tissue adherence. Such coatings may include lubricious silicone materials or repellant omniphobic materials. Such treatments may include hydrophobic surface patternings.

Additionally, or alternatively, removal of excised material 32 may be further enhanced by delivering a fluid such as saline to the treatment site where the cutting occurs to help lubricate and encourage the passage of excised material 32 into internal passageway 20. The fluid may also enhance internal coatings or treatments that prevent tissue adherence. Such coatings may include lubricious, wetted hydrophilic materials. The fluid may also aid in maintaining a desired electrical resistivity and impedance between coring electrode 12 and adjacent tissue 30. For example, elongated body 14 may define one or more optional fluid delivery channels 24 configured to irrigate (indicated by the arrows in FIG. 2A) the cutting site and deliver such fluids to the site during the electro surgical procedure or irrigate internal passageway 20. The delivery of saline to the surgical site may also help introduce a conductive medium to the tissue site for wet field electrosurgery including wet field plasma cutting. However, the introduction of a conductive fluid such a saline may introduce certain drawbacks with the procedures because the fluid can obscure the surgical field and complicate the surgical procedure. Further, if such fluid is used, the fluid must be kept replenished to prevent breakdown in the plasma regime. Also, electric current flowing through the conductive fluid away from the tissue can result in unnecessary power dissipation during cutting or an increase in collateral tissue damage. Tissue associated with joints and discs are typically high in dissolved salts or other ions and hence relatively electrically conductive and may not need further introduction of conductive fluids. Thus, the fluid delivery channels 24 and the delivery of fluids such as saline represent an optional feature and may be used in conjunction with any of the devices described whether or not they are expressly described with such devices or depicted in the accompanying figures.

In some examples, to maintain continuous flow of excised material 32 or help expedite its removal through internal passageway 20, the disclosed electrosurgical devices 10 may also include at least one internal electrode positioned within internal passageway 20. As discussed further below, the internal electrode(s) may be configured to deliver electromagnetic energy to the excised volume of the tissue 32 to further cut, reduce the size, or otherwise break apart the volume of excised tissue 32 initially cut by coring electrode 12, thereby aiding in the conveyance of the volume of the tissue through the internal passageway 20.

Figure 3A:
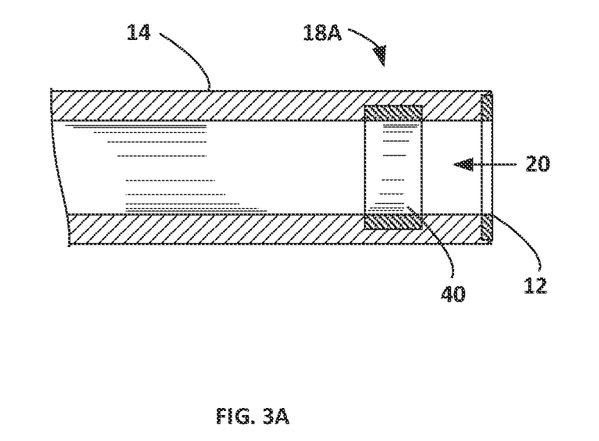
FIGS. 3A and 3B are schematic views of another distal portion of an elongated body that includes a coring electrode as well as at least one internal electrode on the elongated body that may be used with the electrosurgical device of FIG. 1.
Figure 3B:
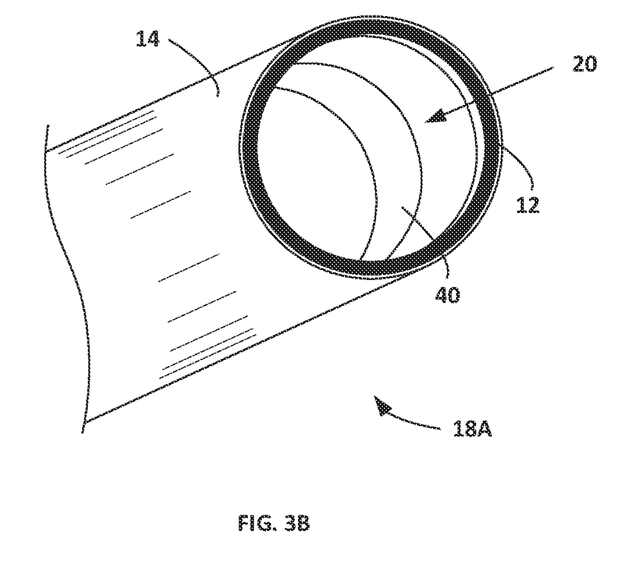

FIGS. 3A and 3B are schematic views including a cross-sectional view (FIG. 3A) and perspective view (FIG. 3B) of another distal portion 18A of an elongated body 14 that can be used with device 10. Distal portion 18A includes coring electrode 12 as well as at least one internal electrode 40 positioned within internal passageway 20. Coring electrode 12 may be as described above and configured to operate in a monopolar configuration with a reference electrode or a bipolar configuration with internal electrode 40 or another electrode on elongated body 14 to cut adjacent tissue.

The bipolar arrangement has the capability of enhancing cutting safety, particularly around nerves and delicate tissue associated with a discectomy procedure, by constraining the electric current to pass between coring electrode 12 and internal electrode 40. The bipolar arrangement may also be used to help coagulate excised or adjacent tissue. Device 10 may be configured to allow the user to select between coagulation and cutting via a switch that activates a suitable electrical signal (typically of different voltage, current, power, frequency, duty-cycle, etc.) for the configuration. Internal electrode 40 may also be used to coagulate, heat or char excised tissue 32 within internal passageway 20 to reduce the tissue's overall size, thereby helping to facilitate its conveyance through internal passageway 20. Coring electrode 12 and internal electrode 40, while located closely adjacent one another, are separated by insulating (dielectric) material of elongated body 14 to prevent shorting. The inclusion of internal electrode 40 may also improve the tactile feedback provided by the device 10 during an electrosurgical procedure by reducing resistance generated by excised tissue 32.

Figure 4A:
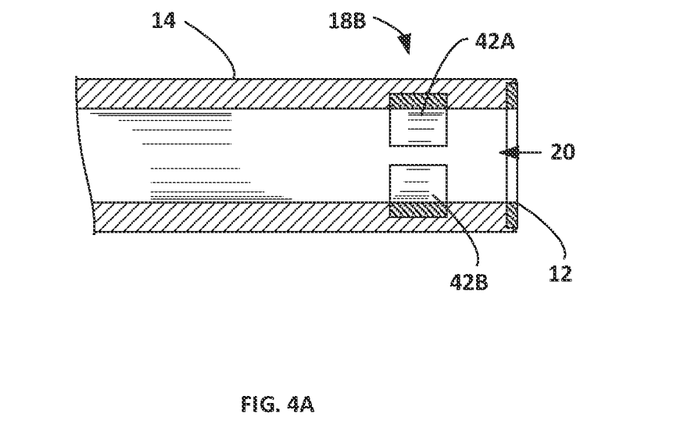
FIGS. 4A and 4B are schematic views of another distal portion of an elongated body that includes a coring electrode and a plurality of internal electrodes on the elongated body that may be used with the electrosurgical device of FIG. 1.
Figure 4B:
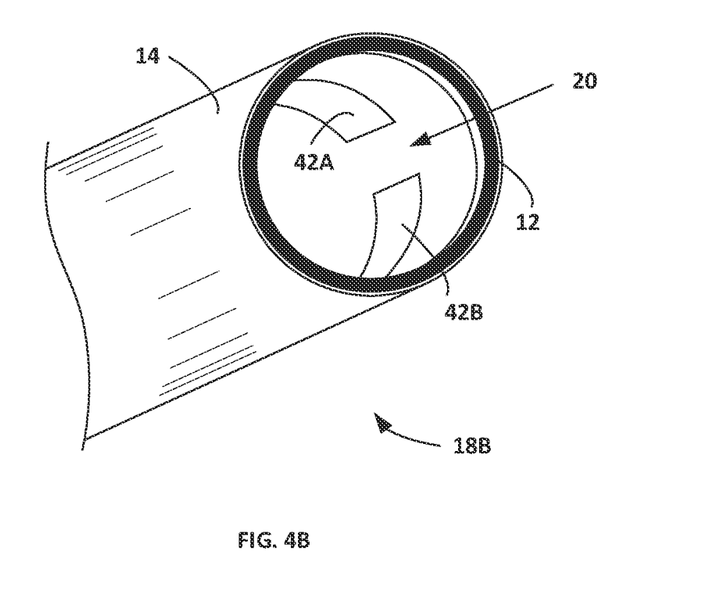

FIGS. 4A and 4B are schematic views including a cross-sectional view (FIG. 4A) and perspective view (FIG. 4B) of another arrangement of a distal portion 18B of an elongated body 14 that may be used with electrosurgical device 10. Distal portion 18B includes coring electrode 12 as well as a plurality of internal electrodes 42A and 42B positioned within internal passageway 20. Coring electrode 12 may be configured to operate in a monopolar or bipolar arrangement as described above with respect to FIGS. 3A and 3B. Additionally, or alternatively, internal electrodes 42A and 42B may be configured to operate in a bipolar configuration therebetween. For example, internal electrodes 42A and 42B may communicate with one another to deliver electromagnetic energy to excised tissue 32 to further breakdown the tissue and reduce the tissue's overall size and volume. The reduced size of excised tissue 32 may be more easily withdrawn from the cutting site through internal passageway 20.

The plurality of internal electrodes 42A and 42B may be in the form of any suitable shape including, but not limited to a partial ring (e.g., partial circular or rectangular ring), curvilinear object, or bar. Further, because the internal electrodes 42A and 42B a positioned within internal passageway 20 and do not directly contact preserved tissue 34, the size and surface area of electrodes 42A and 42B may larger than that of coring electrode 12.

Figure 5A:
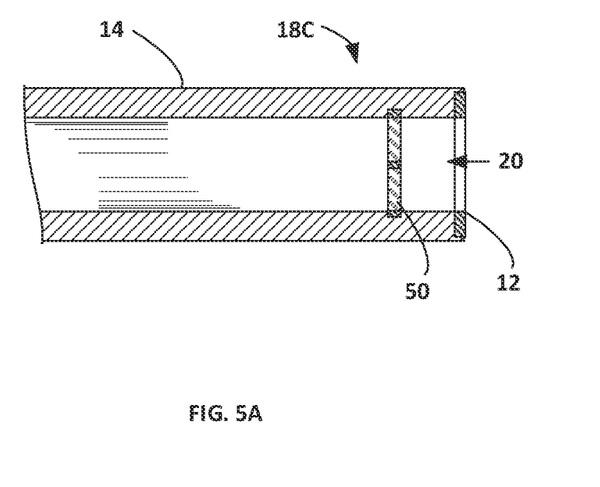
FIGS. 5A and 5B are schematic views of another distal portion of an elongated body that includes a coring electrode and at least one internal cutting electrode configured to further cut excised tissue that may be used with the electrosurgical device of FIG. 1.
Figure 5B:
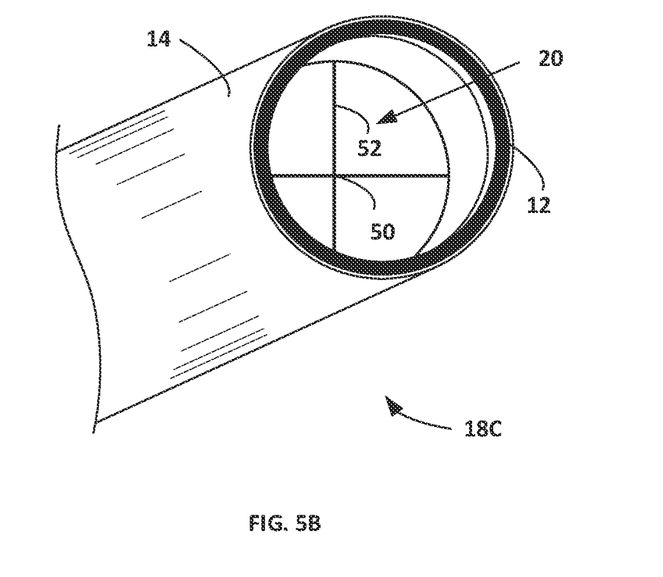

As shown in FIG. 4B, internal electrodes 42A and 42B may be positioned along the inner sidewall of internal passageway 20 so that the electrodes do not impinge on the passageway. However, in some examples, electrosurgical device 10 may include one or more internal electrodes configured to further cut excised tissue 32 (e.g., cut the tissue beyond the cuts produced by coring electrode 12) to help separate excised tissue 32 from tissue 30 by slightly rotating the device 10 along its long axis, break apart the tissue and facilitate its conveyance through internal passageway 20. FIGS. 5A and 5B are schematic views including a cross-sectional view (FIG. 5A) and perspective view (FIG. 5B) of another arrangement of a distal portion 18C of an elongated body 14 that may be used with electrosurgical device 10. Distal portion 18C includes coring electrode 12 as well as an internal cutting electrode 50 positioned within internal passageway 20. Coring electrode 12 may be configured to operate in a monopolar arrangement or in a bipolar arrangement cutting electrode 50, or other electrodes on elongated body 14, in a similar manner to that described above with respect to FIGS. 3A and 3B.

Internal cutting electrode 50 includes at least one cross member 52 that at least partially dissects the cross-section of internal passageway 20. In the illustration shown in FIG. 5B, internal cutting electrode 50 includes at least one cross member 52 that at least partially dissects internal passageway 20. As excised tissue 32 is brought into contact with cross member 52, the member delivers electromagnetic energy to the excised tissue 32 to further cut the tissue longitudinally into multiple pieces. The clinician may then rotate device 10 providing a lateral cut (if needed) that separates the excised tissue 32 from bulk tissue 30.

Internal cutting electrode 50 may be configured to function as a monopolar or bipolar electrode. For example, internal electrode 50 may communicate with coring electrode 12 to deliver electromagnetic energy to excised tissue 32 to further breakdown the tissue and reduce the tissue's overall size and volume. The reduced size of excised tissue 32 may be more easily withdrawn then from the cutting site through internal passageway 20. Cutting electrode 50 may be composed of a wire or rigid structure the impedes on the internal passageway 20 to further dissect excised tissue 32.

Figure 6A:
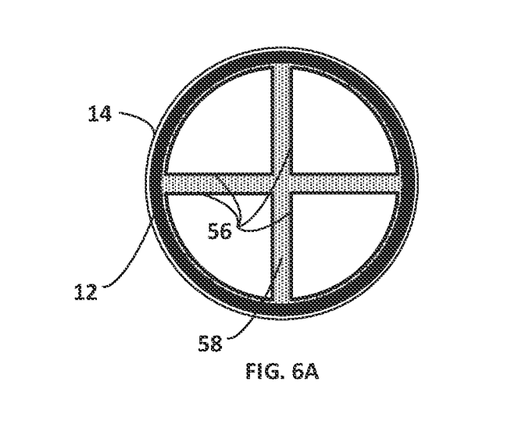
FIGS. 6A to 6C are schematic views of another distal portion of an elongated body that includes a coring electrode and a plurality of internal cutting electrodes configured to further cut excised tissue that may be used with the electrosurgical device of FIG. 1.
Figure 6B:
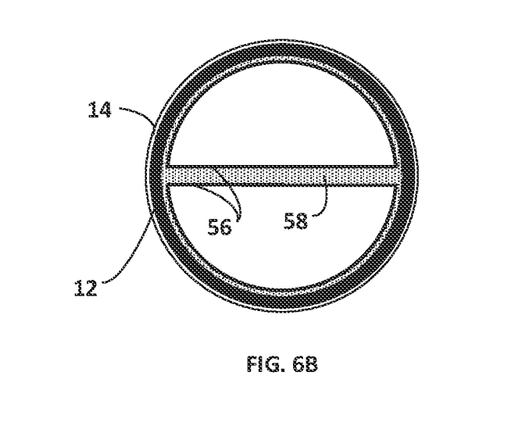
Figure 6C:
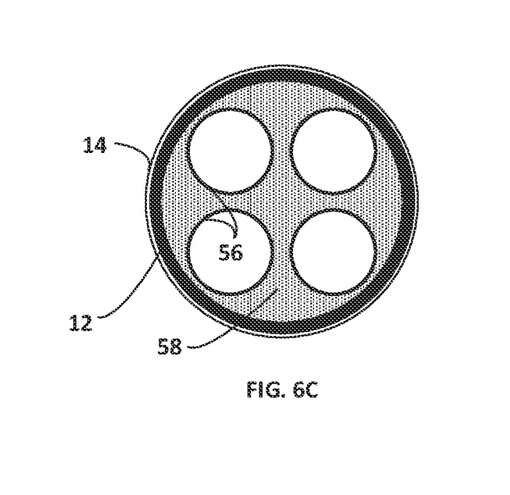

In some examples, internal cutting electrode 50 may be composed of a plurality of electrodes. For example, FIGS. 6A-6C are schematic views of alternative configurations that each include a plurality of internal cutting electrodes 56 of various shapes and sizes. Each internal cutting electrode 56 at least partially dissects the cross-section of internal passageway 20. Electrodes 56 may also define a reduced opening compared to coring electrode 12 such that excised tissue 32 passing by the respective electrode 56 is further cut into pieces, thereby reducing the overall size of the excised tissue and making it easier to be conveyed through internal passageway 20.

The electrode designs may further include one or more rigid support members 58 of dielectric material that both support the portions of cutting electrodes 56 as well as provide electrical insulation between adjacent electrodes 56 such that the electromagnetic energy transmitted by cutting electrodes 56 must travel through excised tissue 32. In some examples, the plurality of internal cutting electrodes 56 and internal support members 58 may be constructed as an insert that is embedded in elongated body 14 such that the insert defines part of the internal passageway 20.

Due to the plurality of internal cutting electrodes 52 being present, the electrodes 56 may be easily configured in a bipolar arrangement relative to one another and/or coring electrode 12 to conveniently cut excised tissue 32. Simple rotation of internal cutting electrodes 56 during the electrosurgical procedure will disconnect excised tissue 32 from bulk tissue 30 as needed.

Figure 7A:
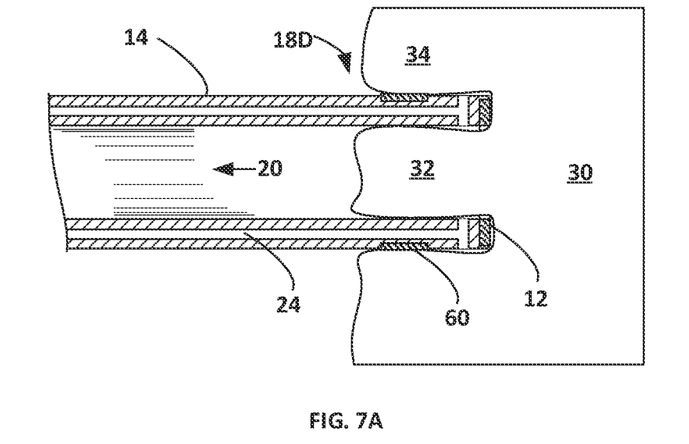
FIGS. 7A and 7B are schematic views of another distal portion of an elongated body that includes a coring electrode and at least one external electrode on the elongated body that may be used with the electrosurgical device of FIG. 1.
Figure 7B:
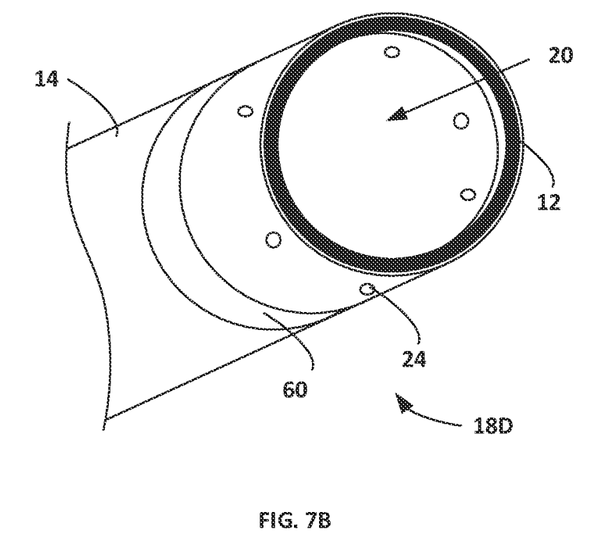

FIGS. 7A and 7B are schematic cross-sectional and perspective views respectively of another arrangement of a distal portion 18D of an elongated body 14 that may be used with electrosurgical device 10. Distal portion 18D includes one or more external electrodes 60 positioned on the exterior surface of elongated body 14. External electrode 60 may be configured to interact with adjacent tissue (e.g., preserved tissue 34) in a variety of configurations to serve one or more uses. For example, external electrode 60 may be configured to operate in a bipolar configuration with one or more of coring electrode 12 or the internal electrodes (if present) to provide field coagulation of the adjacent tissue 34. Additionally, or alternatively, external electrode 60 may be used in a sensing capacity to measure or interrogate one or more properties of adjacent tissue 34 to, for example, enhance the safety capacity of device 10 by providing more accurate feedback of the adjacent tissue such as its electrical resistivity and impedance, composition, or the like.

In some examples, it may be preferable to radially offset coring electrode 12 from the outer diameter defined by elongated body 14 such that as coring electrode 12 traverses through soft tissue 30, it does not contact adjacent tissue 34 that is intended to be preserved throughout the electrosurgical procedure. As such the largest diameter defined by the surface of electrode 12 is less than the outer diameter of distal portion 18 of elongated body 14. In some examples, the radial offset may measure about 0.2 mm to about 4.0 mm as measured in a direction perpendicular to the longitudinal axis of elongated body 14 relative to the widest part of distal portion 18.

Figure 8A:
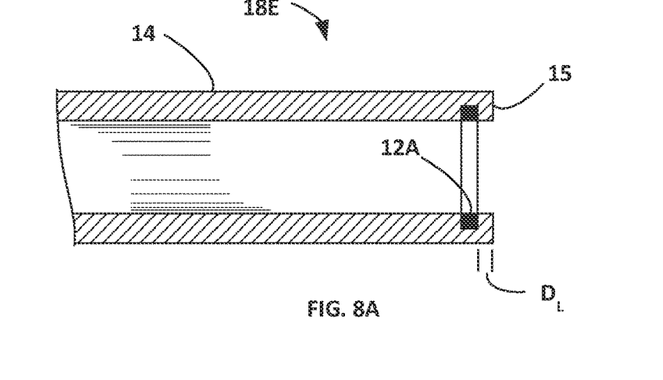
FIGS. 8A-8C are schematic cross-sectional views of another arrangement of a distal portion of an elongated body that may be used with electrosurgical device of FIG. 1 that illustrate a possible offset arrangement for the coring electrode.
Figure 8B:
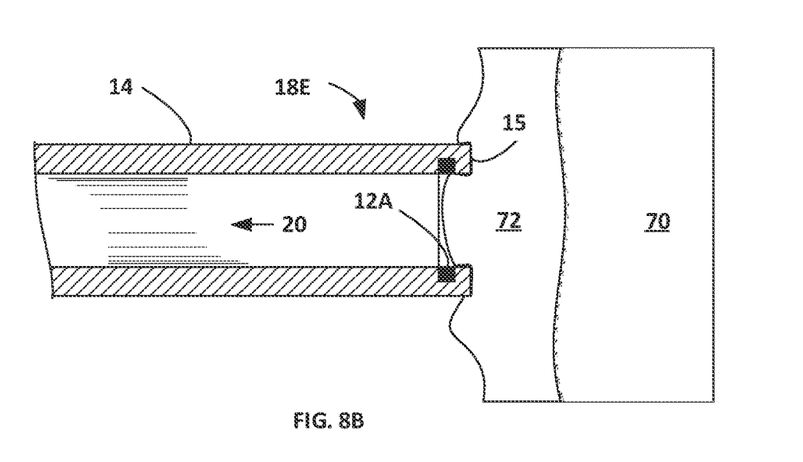
Figure 8C:
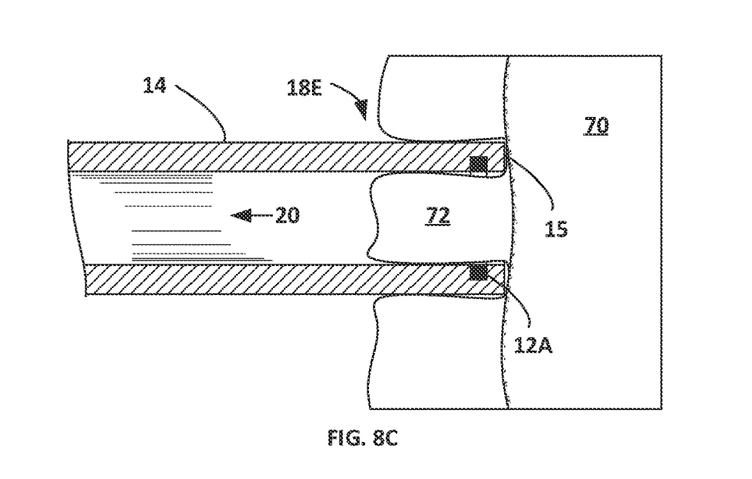

Alternatively, coring electrode 12 may be longitudinally offset so that the electrode does not form part of the distal end (e.g., distal most portion) of elongated body 14. For example, FIGS. 8A-8C are schematic cross-sectional views of another arrangement of a distal portion 18E of an elongated body 14 that may be used with electrosurgical device 10 that illustrate a possible offset arrangement for coring electrode 12A. As shown in FIGS. 8A-8C, coring electrode 12A may be longitudinally offset ($D_L$) from the distal most end 15 of elongated body 14 such that when distal most end 15 is brought into contact with a rigid surface 70, such as bone tissue (e.g., FIG. 8C), the longitudinal offset prevents coring electrode 12A from contacting rigid surface 70, even when forward force is exerted by the user.

In contrast, when contacting soft tissue 72 (e.g., FIG. 8B) intended to be excised, the soft tissue 72 may be deformed and conveyed into opening 20 where the soft tissue contacts coring electrode 12A, thereby allowing soft tissue 72 to be cut and excised in the manner described above. In some examples, the longitudinal offset may measure about 0.1 mm to about 4.0 mm as measured in a direction parallel to the longitudinal axis of elongated body 14 relative to distal end 15.

The radial or longitudinal offset design of coring electrode 12 or 12A may increase the cutting safety of electrosurgical device 10 by increasing tactile feedback and preventing damage to adjacent tissue. Such features may be particularly useful in procedures such as a discectomy where preservation of bone tissue and surrounding blood vessel or nerve clusters is desired.

Figure 9A:
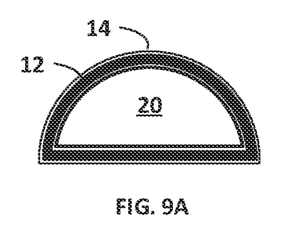
FIGS. 9A-9E are schematic cross-sectional views of optional configurations for the disclosed coring electrode.
Figure 9B:
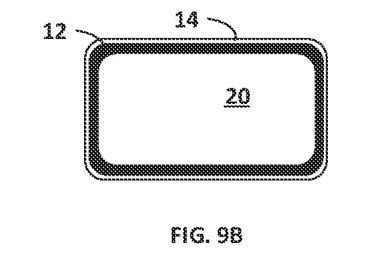
Figure 9C:
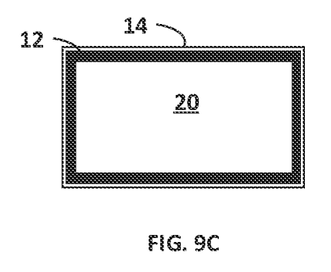
Figure 9D:
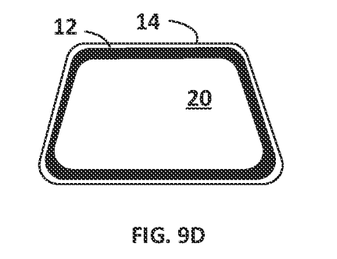
Figure 9E:
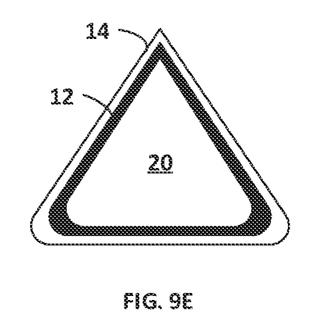

The cross-section of elongated body 14 may take on any suitable shape and size as desired for particular applications. For example, elongated body 14 may possess a circular (e.g., FIG. 2B), semi-circular (e.g., FIG. 9A), oval, curvilinear, rectangular (e.g., FIGS. 9B and 9C), trapezoidal (e.g., FIG. 9D), triangular (e.g., FIG. 9E), or some other multi-faceted cross-sectional shape. In some examples, it may be useful have a combination of curved and straight sides such as the cross-section depicted in FIG. 9A to provide the clinician with multiple edging options for excising tissue. Further the intersections between adjacent sides may themselves be curvilinear (e.g., rounded as depicted in FIG. 9B), abrupt resulting in distinct edge transitions (e.g., the right-angle transition as depicted in FIG. 9C), or a combination of curvilinear and abrupt transitions (e.g., as depicted in FIG. 9E). The selection of cross-sectional shape of elongated body 14, and by association coring electrode 12, may help simultaneously improve tissue removal and tissue preservation in treatment areas having particular size or shape constraints or delicate adjacent tissue that can be easily damaged. Additionally, or alternatively, the distal opening established by coring electrode 12 may be angled relative to the longitudinal access defined by elongated body 14 such that the distal opening does not sit perpendicular to the longitudinal access of elongated body 14. Such non-perpendicular alignment of the distal opening may improve lateral movement of the distal end during tissue removal.

Figure 10A:
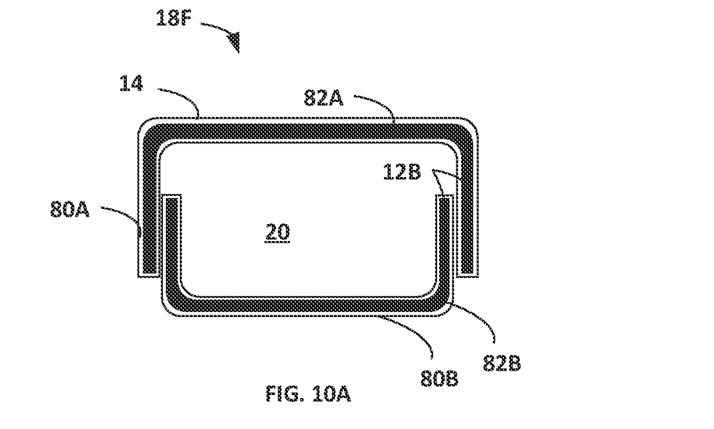
FIGS. 10A and 10B are schematic cross-sectional views of another example distal portion of an elongated body that may be used with the electrosurgical device of FIG. 1 that includes a size-adjustable coring electrode.
Figure 10B:
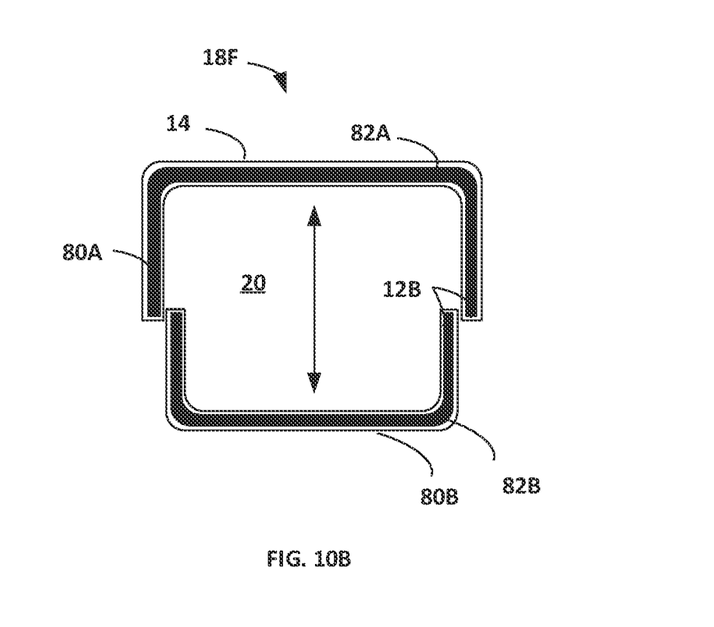

In some examples, electrosurgical device 10 may be configured to have a size-adjustable distal opening. For example, FIGS. 10A and 10B are schematic cross-sectional views of example distal portion 18F of an elongated body 14A that includes a size-adjustable coring electrode 12B. Elongated body 14A includes at least two segments 80A and 80B that are configured to slide laterally relative to one another to increase the cross-sectional area defined by the distal opening. For example, the expanded opening in FIG. 10B may represent an unconstrained configuration and the compressed opening in FIG. 10A may represent a constrained configuration. Actuation between the two configurations may be controlled by a movable exterior sheath that contains the distal opening in the configuration of FIG. 10A.

Each segment 80A and 80B includes a respective electrode segment 82A and 82B of coring electrode 12B that together define an opening into internal passageway 20. The two electrode segments 82A and 82B may be electrically coupled together so as to define a single coring electrode that functions in either a monopolar configuration with a reference electrode or a bipolar configuration with another electrode on elongated body 14A. Alternatively, electrode segments 82A and 82B may be wired independently of one another within device 10 such that the segments 82A and 82B operate in unison (e.g., as a bipolar electrode relative to one another or relative to one or more other electrodes within device 10) to form coring electrode 12B. The transition from a small cross-sectional area (FIG. 10A) to a large cross-sectional area (FIG. 10B) may be mechanically actuated by a trigger mechanism or other suitable mechanism contained within handle assembly 22 allowing the clinician to easily transition between the two sizes. Additionally, or alternatively, the cross-section of distal opening may be any suitable configuration such as rectangular (e.g., as shown in FIGS. 10A and 10B), circular, semi-circular, or rounded, or other configuration.

Various embodiments of systems, devices, and methods have been described herein. These embodiments are given only by way of example and are not intended to limit the scope of the claimed inventions. It should be appreciated, moreover, that the various features of the embodiments that have been described with respect to the different figures may be combined in various ways to produce numerous additional embodiments. For example, variations of the different electrodes may be combined with other internal electrodes, coring electrodes, external electrodes, and combinations thereof to produce an electrosurgical device tailored for a particular application or procedure. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. An electrosurgical device comprising:
an elongated body extending from a proximal portion to a distal portion and defining an internal passageway configured to convey tissue from the distal portion to the proximal portion;
a coring electrode positioned at the distal portion of the elongated body, wherein the coring electrode is at an opening to the internal passageway, and wherein the coring electrode is configured to deliver electromagnetic energy to adjacent tissue to cut a volume of the tissue as the tissue is conveyed into the internal passageway; and
an internal electrode positioned within the internal passageway and configured to deliver electromagnetic energy to the volume of the tissue within the internal passageway to further cut or reduce a size of the volume of the tissue.

2. The electrosurgical device of claim 1, wherein the coring electrode is configured to operate in a monopolar configuration to cut the volume of tissue as the tissue is conveyed into the internal passageway.

3. The electrosurgical device of claim 1, wherein the coring electrode is configured to operate in a bipolar configuration with another electrode on the elongated body to cut or ablate soft tissue.

4. The electrosurgical device of claim 1, wherein the coring electrode is longitudinally offset from a distal end of the elongated body so that a distal most surface of electrosurgical device is not defined by the coring electrode.

5. The electrosurgical device of claim 1, wherein the internal electrode comprises a plurality of internal electrodes configured to operate in a bipolar configuration relative to each other to deliver electromagnetic energy to reduce the size of the volume of the tissue conveyed into the internal passageway.

6. The electrosurgical device of claim 1, wherein the internal electrode comprises a cross member that least partially dissects the internal passageway and is configured to deliver electromagnetic energy to further cut the volume of the tissue conveyed into the internal passageway.

7. The electrosurgical device of claim 1, comprising a plurality of internal electrodes, wherein each of the plurality of internal electrodes at least partially dissect the internal passageway and are configured to operate in a bipolar configuration relative to each other to deliver electromagnetic energy to further cut the volume of the tissue conveyed into the internal passageway.

8. The electrosurgical device of claim 7, wherein the plurality of internal electrodes each define a smaller opening compared to the coring electrode.

9. The electrosurgical device of claim 7, wherein the plurality of internal electrodes are supported by a dielectric material that spans at least a portion of the internal passageway.

10. The electrosurgical device of claim 1, further comprising an external electrode on the distal portion of the elongated body and defining an outer surface of the electrosurgical device, wherein the external electrode is configured to function in a bipolar configuration relative to the coring electrode or the internal electrode.

11. The electrosurgical device of claim 1, wherein the elongated body defines a least one fluid delivery channel configured to deliver a fluid to the distal portion adjacent to the coring electrode.

12. The electrosurgical device of claim 1, further comprising a handle assembly coupled to the proximal portion of the elongated body and configured to couple to an electrosurgical power supply that delivers the electromagnetic energy to the coring electrode and the internal electrode.

13. The electrosurgical device of claim 12, wherein the handle assembly comprises a switch configured to select between a bipolar and a monopolar configuration that includes the coring electrode.

14. The electrosurgical device of claim 1, wherein the electrosurgical device is configured to be coupled to a negative pressure source to provide suction of the volume of the tissue through the internal passageway.

15. The electrosurgical device of claim 1, wherein the distal opening size-adjustable that selectably transitions from a first size to a second size defining a larger distal opening.

16. The electrosurgical device of claim 1, wherein the coring electrode is configured to deliver electromagnetic energy as continuous or pulsed radio frequency electromagnetic energy.

17. The electrosurgical device of claim 1, wherein the coring electrode is configured to deliver electromagnetic energy as electric fields, electric currents, or electric plasmas including ion, electron, and electron avalanche plasmas.

18. The electrosurgical device of claim 1, wherein an internal electrode and the coring electrode are configured to sense electromagnetic properties including electrical resistance or impedance of tissues between or beside the bipolar electrodes.

19. An electrosurgical device comprising:
an elongated body extending from a proximal portion to a distal portion and defining an internal passageway configured to convey tissue from the distal portion to the proximal portion;
a coring electrode positioned at the distal portion of the elongated body, wherein the coring electrode is at an opening to the internal passageway, wherein the coring electrode is configured to deliver electromagnetic energy to adjacent tissue to cut a volume of the tissue as the tissue is conveyed into the internal passageway, and wherein the coring electrode is longitudinally offset from a distal end of the elongated body so that a distal most surface of electrosurgical device is not defined by the coring electrode; and
an internal electrode positioned within the internal passageway and configured to deliver electromagnetic energy to the volume of the tissue within the internal passageway to further cut or reduce a size of the volume of the tissue.

20. The electrosurgical device of claim 19, wherein the coring electrode is configured to operate in a monopolar configuration to cut the volume of the tissue as the tissue is conveyed into the internal passageway.

21. The electrosurgical device of claim 19, further comprising:
an external electrode on the distal portion of the elongated body and defining an outer surface of the electrosurgical device,
wherein the coring electrode is configured to operate in a bipolar configuration with the internal electrode or the external electrode to cut or ablate adjacent tissue.

22. The electrosurgical device of claim 21, wherein the internal electrode comprises a cross member that least partially dissects the internal passageway and is configured to deliver electromagnetic energy to further cut the volume of the tissue conveyed into the internal passageway.

23. The electrosurgical device of claim 22, comprising a plurality of internal electrodes, wherein each of the plurality of electrodes define a smaller opening compared to the coring electrode and are configured to deliver electromagnetic energy to further cut the volume of the tissue conveyed into the internal passageway.

24. A method of performing electrosurgery on soft tissue comprising,
delivering electromagnetic energy to adjacent tissue using a coring electrode of an electrosurgical device to cut a volume of the tissue, wherein the electrosurgical device comprises an elongated body extending from a proximal portion to a distal portion and defining an internal passageway configured to convey tissue from the distal portion to the proximal portion, the coring electrode positioned at the distal portion of the elongated body, and an internal electrode positioned within the internal passageway, wherein the coring electrode cuts the volume of the tissue as the tissue is conveyed into the internal passageway; and
delivering electromagnetic energy within the internal passageway using the least one internal electrode to further cut or reduce the size of the volume of the tissue cut by the coring electrode to facilitate the conveyance of the volume of the tissue through the internal passageway.

* * * * *